United States Patent
Schick et al.

(10) Patent No.: US 6,312,154 B1
(45) Date of Patent: Nov. 6, 2001

(54) METHOD FOR ON-LINE MEASUREMENT OF FUEL HEAT CONTENT OF FUEL IN A COMBUSTION TURBINE SYSTEM

(75) Inventors: Louis Andrew Schick, Delmar; Douglas Ancona Catharine, Scotia; Stephen Duane Sanborn, Copake, all of NY (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/483,964

(22) Filed: Jan. 18, 2000

(51) Int. Cl.$^7$ ............................ G01N 25/22; G01N 25/20
(52) U.S. Cl. ........................... 374/36; 374/43; 374/44
(58) Field of Search ................................ 374/36, 43, 44

(56) References Cited

U.S. PATENT DOCUMENTS

| | | | |
|---|---|---|---|
| 4,386,858 | * 6/1983 | Kude et al. | 374/37 |
| 5,617,719 | * 4/1997 | Ginter | 60/39.03 |
| 5,743,079 | * 4/1998 | Walsh et al. | 60/39.03 |
| 5,807,749 | * 9/1998 | Hornemann | 374/36 |
| 5,882,115 | * 3/1999 | Vander Heyden et al. | 374/36 |
| 5,892,145 | * 4/1999 | Moon et al. | 73/118.2 |
| 6,050,093 | * 4/2000 | Daudel et al. | 60/602 |
| 6,244,097 | * 6/2001 | Schley et al. | 374/36 |

* cited by examiner

Primary Examiner—Christopher W. Fulton
Assistant Examiner—Yaritza Guadalupe
(74) Attorney, Agent, or Firm—John F. Thompson; Jill M. Breedlove

(57) ABSTRACT

The fuel heat content of fuel is measured on-line while a combustion turbine system is running by measuring data from the combustion turbine system during combustion of the fuel. The measured data are corrected using a standard correction algorithm. The fuel heat content of the fuel is determined using at least a portion of the corrected data. From the measurement of the fuel heat content, any changes in the fuel heat content are determined. Also, any changes in the control and operational parameters attributable to the change in fuel heat content are determined.

12 Claims, 3 Drawing Sheets

METHOD FOR ON-LINE MEASUREMENT OF FUEL HEAT CONTENT OF FUEL IN A COMBUSTION TURBINE SYSTEM

BACKGROUND OF THE INVENTION

The present invention relates to measuring fuel heat content of fuel, and more particularly, to measuring fuel heat content while a combustion turbine system is on-line and/or running.

The measurement of the fuel heat content of fuel is an important factor in controlling the combustion of the fuel. However, in a deregulated power generation market, it is desirable that power production be as inexpensive as possible. In an effort to produce inexpensive power, typically, the most inexpensive fuel is used. Unfortunately, these inexpensive fuels have fuel heat content that varies dramatically from the rated heating value of the fuel. Therefore, controlling the combustion of these inexpensive fuels has become increasingly complex.

Typically, the fuel heat content is measured by performing various tests on the fuel in a laboratory or other controlled setting. These tests can include calorimetric, stoichiometric, constituent analysis and catalytic combustion. In general, the laboratory tests provide a fuel heat content measurement for the fuel under controlled conditions and do not provide an on-line determination of the fuel heat content while the combustion turbine system is on-line and running. An on-line measurement of the fuel heat content would allow the control parameters associated with the combustion turbine system to be adjusted such that the maximum operational efficiency of the combustion turbine system is achieved. In addition, an on-line measurement of the fuel heat content would allow control parameters associated with the combustion turbine system to be adjusted to avoid damage or increased wear caused by the changes of temperature and pressure in the combustion turbine system that are associated with a change in the fuel heat content. Therefore, a need exists for a method of measuring the fuel heat content while the combustion turbine system is on-line and running.

Presently, fuel heat content monitors are available that can measure the fuel heat content while the system is on-line. The fuel heat content monitor is a separate device that requires installation and additional data monitoring. However, these fuel heat content monitors are expensive. As such, in an effort to produce energy at the lowest price, the added cost of these fuel heat monitors and the cost associated with monitoring the heat fuel content data makes the use of the heat fuel content monitors impractical. Therefore, a need also exists for a method of measuring fuel heat content that does not require the purchasing of expensive equipment. Also, a need exists for a method of measuring fuel heat content that uses conventionally monitored data and does not entail the costs associated with additional data monitoring.

In combustion turbine systems, many control and operational parameters are measured, such as, but not limited to, temperature, pressure and fuel flow. Typically, changes in the fuel heat content result in changes in the measured parameters. During monitoring of these parameters, it is important that any change in these measured parameters that is attributable to changes in the fuel heat content be readily determined. Such a determination can prevent unrequired maintenance on the combustion turbine system. Since unrequired maintenance can increase the cost of the power generation, it is desirable that only required maintenance be performed on the combustion turbine system in order to keep the power generation costs to a minimum. Therefore, a need exists for an on-line measurement of the fuel heat content that determines whether changes in the control and operational parameters are attributable to changes in the fuel heat content.

BRIEF SUMMARY OF THE INVENTION

An exemplary embodiment of the present invention provides a method for determining a change in fuel heat content of fuel used in a combustion turbine system. The method includes measuring data from the combustion turbine system during combustion of the fuel while the combustion turbine system is on-line and running. The measured data is corrected using a standard correction algorithm. A heat rate is calculated using at least a portion of the corrected data. A change in the calculated heat rate is determined. A compressor efficiency and a pressure ratio is calculated using at least a portion of the corrected data. The calculation of the compressor efficiency and the pressure ratio is based on the determination of a change in the calculated heat rate. A change in the calculated compressor efficiency and the calculated pressure ratio is determined. A temperature rise across a hot section of the combustion turbine system is calculated using at least a portion of the corrected data. The calculation of the temperature rise across the hot section is based on the determination of a change in the compressor efficiency and the pressure ratio. A change in the temperature rise across the hot section of the combustion turbine system is determined. A fuel heat content is calculated using at least a portion of the corrected data. The calculation of the fuel heat content is based on the determination of a change in the temperature rise across the hot section. A change in the fuel heat content is calculated, and a mathematical model of the operation of the combustion turbine system is changed based on the determination of a change in the fuel heat content.

Advantageously, the method described hereinabove measures the fuel heat content of fuel while a combustion turbine system is on-line and running, and the method measures the fuel heat content without the purchasing of expensive equipment. Also, the method described hereinabove measures fuel heat content using conventionally monitored data and does not entail the costs associated with additional data monitoring. Further, the method described hereinabove provides an on-line measurement of the fuel heat content that determines whether changes in the control and operational parameters are attributable to changed in the fuel heat content.

DETAILED DESCRIPTION OF THE INVENTION

Exemplary embodiments of the present invention involve a method for determining the fuel heat content and/or changes in the fuel heat content of fuel used in a combustion turbine system 100 (FIG. 1) while the combustion turbine system 100 is on-line and running. The fuel heat content is a desirable factor in controlling the combustion of fuel. The measurement of the fuel heat content provides the amount of fuel required to produce a measurable amount of energy, such as, the amount of fuel required to generate a kilowatt hour (kwh) of power measured in, for example, gallons/kwh, liters/kwh or cubic centimeters/kwh. In this disclosure, the measurement of the amount of fuel required to produce a measurable amount of energy is called fuel heat content, but, in the art, this measurement can also be referred to as heating value, such as, low heating value (LHV) and high heating value (HHV).

Figure 1:
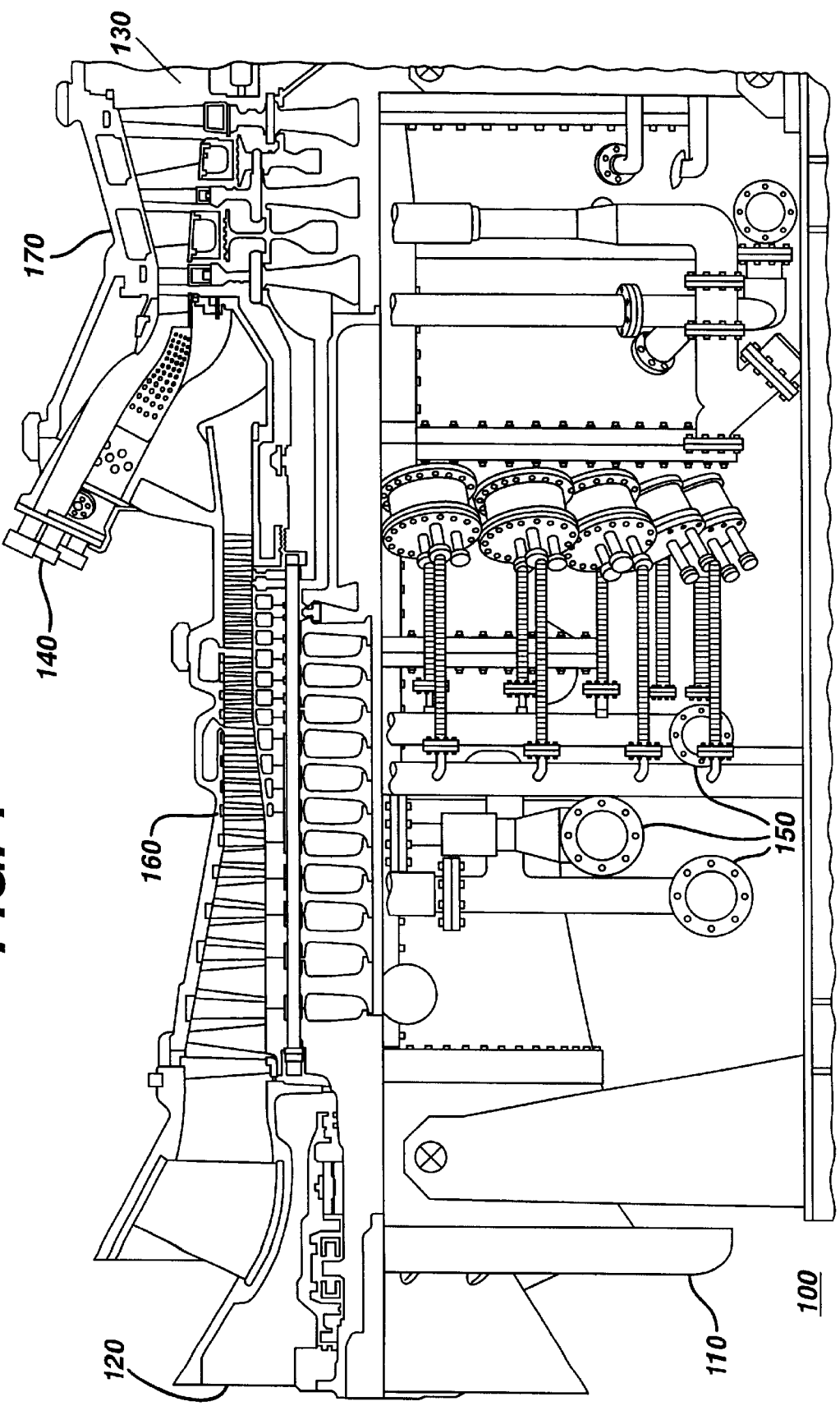
FIG. 1 is a highly simplified side view and cut away view of one embodiment of a combustion turbine system useful for illustrating exemplary embodiments of the present invention.

In FIG. 1, a highly simplified combustion turbine system 100 comprises a gas turbine 110. It should be appreciated that the present invention is not limited to a gas turbine 110 and includes all combustion turbine systems 100 that consume fuel to operate. In one embodiment, the gas turbine 110 uses natural gas as a fuel. However, it should be appreciated that the fuel in other combustion turbine systems 100 is not limited to natural gas. Other suitable fuels may, for example, include gasoline, kerosene, diesel fuel, wood, coal and jet fuel.

As shown in FIG. 1, the gas turbine 110 includes an inlet port 120 and an exit port 130. The inlet port 120 is the location where a combustion gas is introduced into the combustion turbine system 100. The combustion gas is combined with the fuel in the combustion turbine system 100. The fuel and the combustion gas are combined in a ratio that is known in the art and can be controlled via control parameter s of t he combustion turbine system 100. In one embodiment, the combustion gas comprises air. The exit port 120 is the location where the exhaust from the gas turbine 110 exits the combustion turbine system 100. In one embodiment, the exhaust gas includes various end products of the combustion process that is carried out in the combustion turbine system 100.

The combustion gas is provided to a compressor 160. The fuel is provided via fuel inlets 150 to the compressor 160. The fuel inlets 150 are controlled by fuel flow controls 140. The combustion gas and the fuel are mixed in the compressor 160 and supplied to a hot section 170. In the hot section 170, the combination of the fuel and the combustion as is ignited, and the exhaust is fed to the exit port 130 after the combustion has taken place. The combusted fuel mixture produces a desired form of energy, such as, for example, electrical, heat and mechanical energy. In one embodiment, the combusted fuel mixture produces electrical energy measured in kilowatt hours (kwh). However, the present invention is not limited to the production of electrical energy and encompasses other forms of energy, such as, mechanical work and heat.

The combustion turbine system 100 is typically controlled via various control parameters from an automated and/or electronic control system (not shown) that is attached to the combustion turbine system 100. A detailed description of the automated and/or electronic control system (not shown) that controls the combustion turbine system 100 is beyond the scope of this disclosure. However, it should be appreciated that the determination of the fuel heat content and changes in the fuel heat content can be supplied to the automated and/or electronic control system (not shown) to be used for control calculations or mathematical control model algorithms used to control the combustion turbine system 100.

Figure 2:
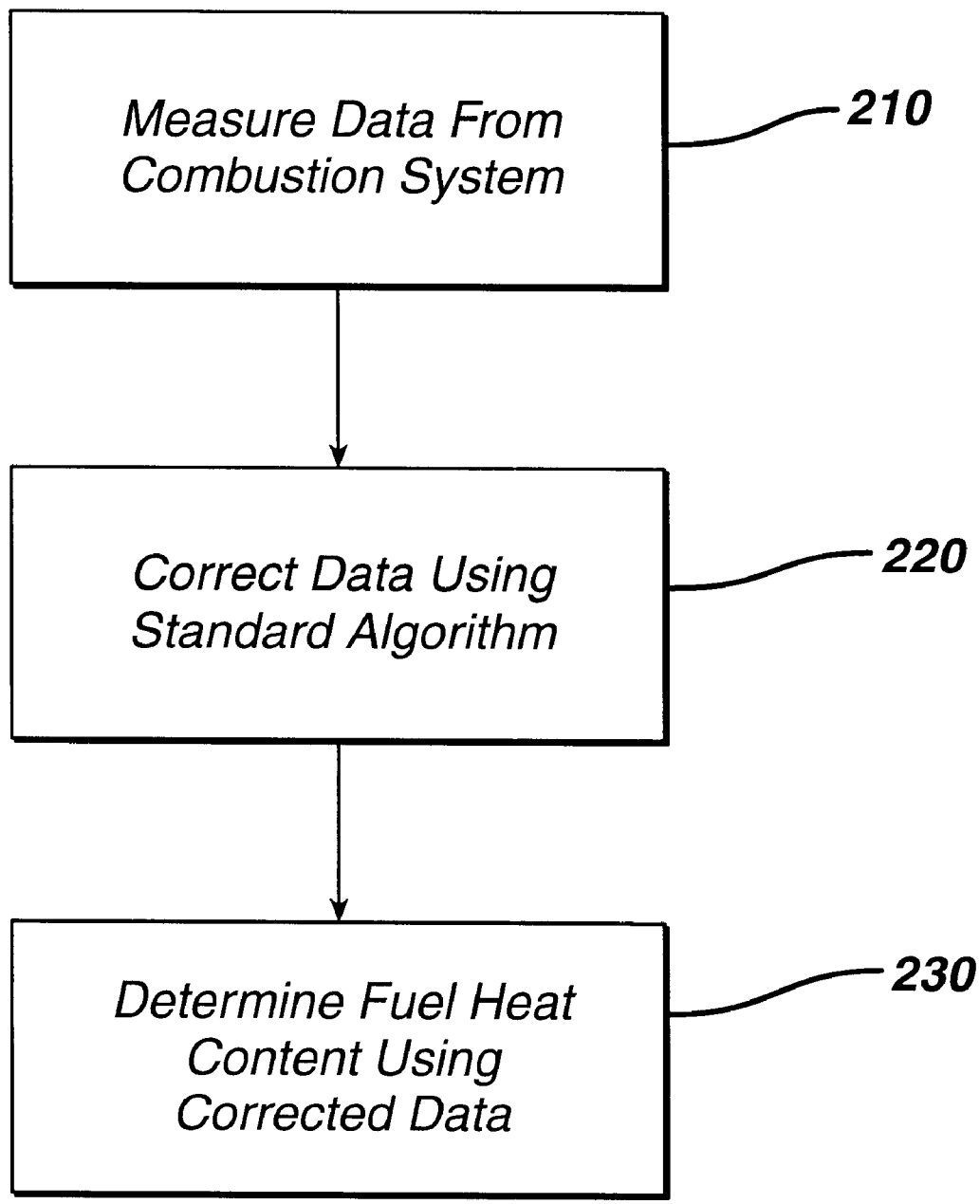
FIG. 2 is a flow chart of one embodiment of an exemplary method of the present invention for determining the fuel heat content of fuel used in a combustion turbine system such as that of FIG. 1.

As shown in FIG. 2, one embodiment of a method for on-line determination of fuel heat content of fuel used in combustion turbine system 100 (FIG. 1) includes measuring data from the combustion turbine system 100 while the combustion turbine system 100 is on-line and running (step 210). The measured data is corrected using a standard correction algorithm (step 220). The fuel heat content is determined using the corrected data (step 230).

In the combustion turbine system 100, data are measured (step 210) from a variety of areas in and on the gas turbine 110 (FIG. 1). The measurement of the data provides information relating to the operation of the combustion turbine system 100. From these data measurements, the combustion turbine system is controlled to maximize the operational efficiency of the combustion turbine system 100. It should be appreciated that the measurement of the data is taken in real-time while the combustion turbine system 100 is on-line and running. The on-line measurement of the data allows various control parameters to be adjusted in real-time such that the combustion turbine system operates at the maximum operational efficiency at all times. In addition, the measured data can be collected such that statistical modeling and analysis can be performed on the measured data, as will be described herein below. In this case, the measured data are sampled per predetermined time periods and these measurements are archived for analysis.

In the combustion turbine system 100 as shown in FIG. 1, the measurement of the data includes measuring a flange to flange output in the gas turbine 110. The flange to flange output is measured on a generator (not shown) of the gas turbine 110. The power that is extracted by the gas turbine 110 drives the compressor 160 and the generator (not shown). The flange to flange output is the electrical power that is made by the generator (not shown). In particular, the flange to flange output is the power generated from the gas turbine 110 less any excitation and/or compressor 160 usage. A fuel flow into the gas turbine 110 from the fuel inputs 150 is measured by transducers (not shown) in the area of the fuel flow controls 140. The fuel flow measures the amount of fuel that is provided to the gas turbine 110 over a specified period of time.

A heating value of the fuel is assumed. In one embodiment, the heating value is not a measured quantity of data but is assumed to be the heating value rating provided by the supplier of the fuel. Typically, the supplier provides a heating value, as part of the fuel specifications, such as, a low heating value (LHV) and a high heating value (HHV). In a preferred embodiment, the assumed heating value is the low heating value (LHV).

The inlet temperature and pressure of the combustion gas are measured at inlet port 120. In addition, the relative humidity of the combustion gas can be measured at the inlet port 120. The outlet temperature and pressure are measured at the exit port 130. It should be appreciated that these temperature, pressure and humidity measurements are provided by transducers that are attached on or near the combustion turbine system 100. More particularly, the transducers (not shown) are respectively positioned near the inlet port 120 and exit port 130. The data measurements can be provided using devices known in the art including, for example, transducers, flow meters, sensors, thermocouples, thermistors and other electronic measuring devices.

The temperature at the outlet of the compressor 160 is measured. In addition, the exhaust temperatures of the gases exiting the hot section 170 are also measured. It should be appreciated that the exhaust temperature at the hot section 170 and the outlet temperature at the exit port 130 can comprise the same measurement in one embodiment of the present invention. In addition, the present invention may encompass data measured from and around the combustion turbine system 100 that are different than the data described herein.

As illustrated in FIG. 2, once the data are measured (step 210) from the combustion turbine system 100 (FIG. 1), the data are corrected using a standard correction algorithm (step 220). The measured data are corrected using the standard correction algorithm to remove any anomalies in the data caused by ambient conditions under which the combustion turbine system 100 is operating. In addition, the correction of the measured data allows all data to be compared regardless of the ambient conditions under which the data were collected. For example, in one embodiment, the standard correction algorithm corrects the data based on the ambient temperature, pressure, relative humidity and elevation. It should be appreciated that other ambient conditions can be used with the standard correction algorithm. It should also be appreciated that the ambient conditions are measured in a similar manner to all measured data, such as, using various sensors and other data collection devices.

As mentioned above, the correction of the measured data is provided so that the data measured on different days can be compared. The data are corrected based on certain ambient conditions to reflect a standard day. The standard day and standard correction algorithm can be measured and determined by a standards organization, such as, the international standards organization (ISO). In addition, as an alternative to using correction information of a standards organization, it should be appreciated that a correction algorithm and standard day can be calculated by sampling and measuring data over various conditions to provide the correction information and, thus, the correction information need not be supplied by a standards organization.

After the measured data are corrected (step 220), the corrected data or a portion of the corrected data are used to determine the fuel heat content (step 230) of the fuel used in the combustion turbine system 100 (FIG. 1). The fuel heat content is determined via a calculation. The calculation of the fuel heat content uses a calculated value of the heat rate ($HR_{new}$) and a previously calculated heat rate ($HR_{old}$). Since the calculation of the heat rate is made in real time while the gas turbine 110 is operating, the calculated values of the heat rate ($HR_{new}$) and ($HR_{old}$) are continually being calculated and are available for the calculation of the fuel heat content. The calculation for the heat rate is further explained herein below. The fuel heat content (FHC) is calculated using the following algorithm:

$$\text{FHC (new)} \approx \frac{\text{HRold}}{\text{HRnew}}$$

In one embodiment, the fuel heat content is provided to a mathematical model of the combustion turbine system 100. The mathematical model is used to control the combustion turbine system 100 to provide the highest operational efficiency. In controlling the combustion turbine system 100, various parameters can be adjusted, such as, the fuel flow, the ratio mixture of the fuel to the combustion gas and the compression of the fuel mixture. It should be appreciated that other parameters can be used during control of the combustion turbine system 100 and the present invention is not limited to only those parameters described herein.

In addition, the determination of the fuel heat content can be used to provide fuel heat content data for statistical modeling and analysis. In this case, the fuel heat content is determined on a predetermined time basis and archived for analysis/modeling purposes. It should be appreciated that the determination of fuel heat content is provided in real-time while the combustion turbine system 100 is on-line and operating. This real-time feedback of the fuel heat content allows control parameters to be adjusted to maximize the operational efficiency of the combustion turbine system 100.

In the exemplary methods described herein, various data are compared to determine whether a change in the data has occurred. The determination of a change is provided by measuring or calculating the data and providing statistical analysis and modeling of the measured and/or calculated data. The measured and/or calculated data are archived in, for example, a database. Noise boundaries are calculated based on an historical analysis of the measured and/or calculated data. The noise boundaries include control limits that are calculated based on statistical analysis, and the noise boundaries provide a boundary in which the data can vary and still be statistically within the limits. A change is determined to occur if the measured and/or calculated data fall outside the control limits of the noise boundaries. It should be appreciated that all types of statistical analysis and modeling are encompassed by the present invention. It should also be appreciated that the determination of a change in various measured and/or calculated data avoids unrequited maintenance from being done on the combustion turbine system 100. In this regard, the determination of changes in measured and/or calculated data can result in finding the portion of the combustion turbine system that is the cause of the change, and therefore, maintenance can be limited to that certain portion of the combustion turbine system 100, or the mathematical model can be altered to reflect the change in the data. Specifically, in one embodiment of the present invention, data are measured and data are calculated to determines changes in the operation of the combustion turbine system 100 that can be attributable to a change in the fuel heat content.

Figure 3:
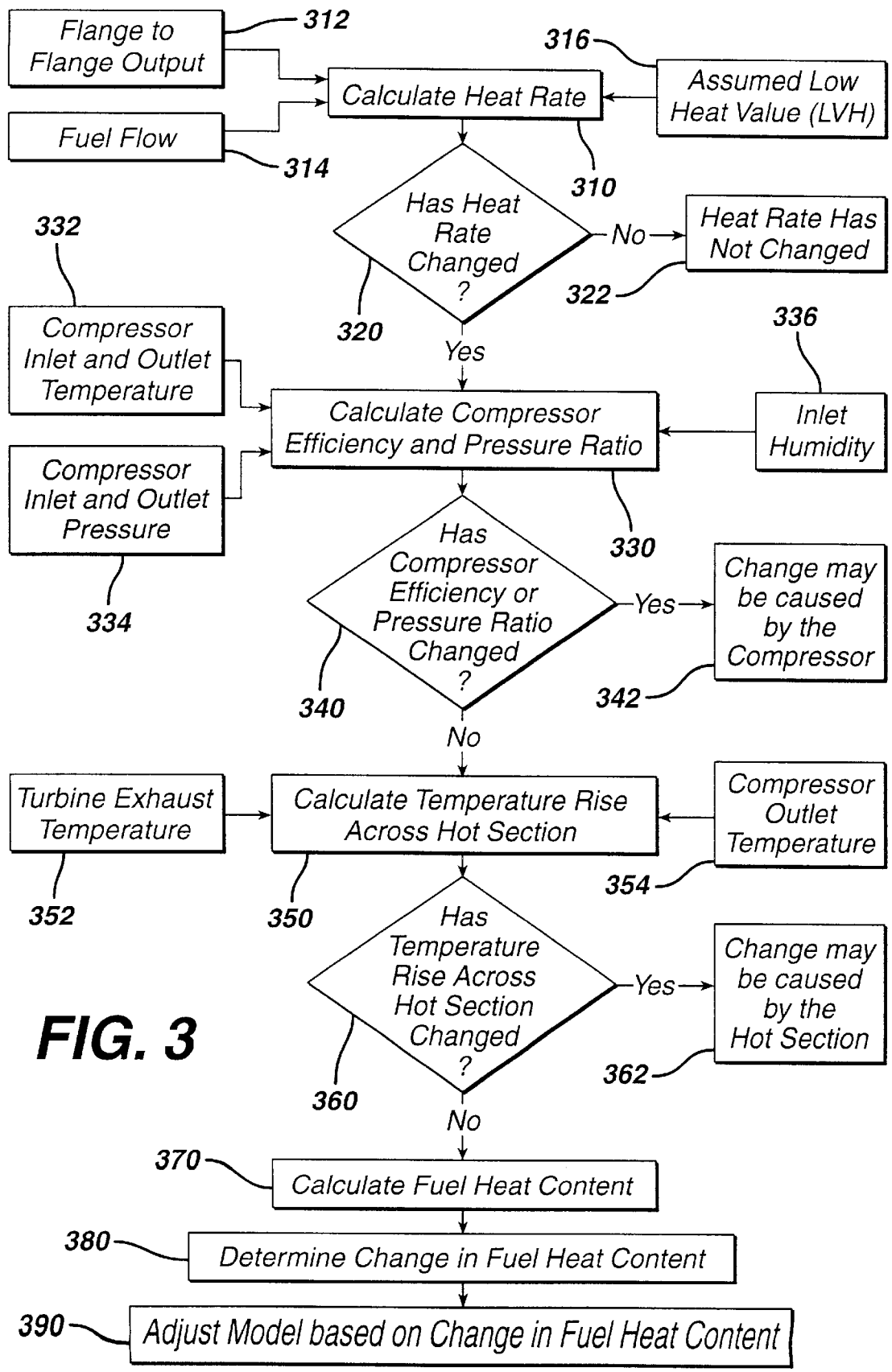
FIG. 3 is a flow chart of one embodiment of an exemplary method of the present invention for determining a change is the fuel heat content of fuel used in a combustion turbine system such as that of FIG. 1.

In FIG. 3, the determination of a change in the fuel heat content includes a calculation of the heat rate (step 310). The heat rate is a determination on the efficiency of the operation of the entire combustion turbine system 100 (FIG. 1). The heat rate (HR) is calculated using the inputs of the flange to flange output (FFO) (step 312), the fuel flow (FF) (step 314) and the low heat value ($LHV_{assumed}$) which is assumed. The heat rate is calculated using the following algorithm:

$$HR = \frac{FF \cdot LHVassumed}{FFO}$$

The assumed LHV may comprise the heating value supplied by the fuel supplier. The fuel supplier calculates the LHV using various techniques know in the art. It should be appreciated that the fuel supplier can provide a LHV and a high heating value (HHV) with the fuel. In another embodiment, the assumed heating value can be the HHV or another heating value that has been calculated from various other data. In addition, as described above, the measured data used to calculate the heat rate are corrected using a correction algorithm.

In addition, the heat rate can be calculated if the heat losses in the compressor 160 (FIG. 1), the gas turbine 110 and the generator (not shown) are known. For example, the algorithm for the heat rate (HR) can be as follows:

$$HR = \frac{\text{Power Output} + \text{Compressor loss} + \text{Turbine loss} + \text{Generator loss}}{\text{Power Output}}$$

In this embodiment, the power output is the flange to flange output (FFO). Also, if the power output, compressor loss, turbine loss and generator loss are known, any change in the heat rate can be attributable to the fuel heat content. For example, if the power output and all other heat losses remain constant but the heat rate increases one percent (1%), the actual fuel heat content is one percent (1%) less than the assumed LHV or the previously calculated fuel heat content.

Once the heat rate has been calculated from the corrected data, a determination is made as to whether the heat rate has changed (step 320). The determination of a change in the heat rate is accomplished, as described above, using statistical analysis of the heat rate data. If the calculated heat rate falls outside the control limits of the noise boundaries, the heat rate has not changed (step 322), and no operational anomalies relating to the operation of the combustion turbine system 100 exist.

If the heat rate has changed, a compressor efficiency and a compressor pressure ratio ($P_{ratio}$) are calculated (step 330). Therefore, the calculation is based on the determination of a change in the heat rate. The compressor efficiency provides the operational efficiency of the compressor 160 (FIG. 1). The compressor pressure ratio ($P_{ratio}$) provides the ratio of the inlet to the exit pressures to the compressor 160. These calculated parameters determine if a problem exits within the compressor 160 that is causing the change in the heat rate.

The calculation of the compressor efficiency and the compressor pressure ratio ($P_{ratio}$) uses the inputs of the compressor inlet and outlet temperatures (step 332), the compressor inlet and outlet pressures (step 334) and the relative humidity (step 336). It should be appreciated that the measured data used to calculate the compressor efficiency and the compressor pressure ratio ($P_{ratio}$) are corrected with a correction algorithm, as described above. The calculation of the compressor efficiency is calculated by the ratio of an actual efficiency to an adiabatic efficiency which are calculated using the inlet and out temperatures, inlet and outlet pressures and any change in entropy and/or free energy. In addition, the compressor pressure ratio ($P_{ratio}$) is calculated using the ratio of the outlet pressure to the inlet pressure.

Once the compressor 160 efficiency and the compressor pressure ratio ($P_{ratio}$) have been calculated, a determination is made as to whether the compressor efficiency and the compressor pressure ratio ($P_{ratio}$) have changed (step 340). The determination of the change of the compressor efficiency and the compressor pressure ratio ($P_{ratio}$) (step 340) involves comparing the calculated compressor efficiency and the calculated compressor pressure ratio ($P_{ratio}$), respectively, with the statistical analysis of previously calculated compressor efficiency and the compressor pressure ratio ($P_{ratio}$). If the calculated compressor efficiency or calculated the compressor pressure ratio ($P_{ratio}$) fall outside the control limits of the noise boundaries, a problem may exist in the compressor 160 that is causing the change in the heat rate.

If no change in the compressor efficiency or the compressor pressure ratio ($P_{ratio}$) exists, a problem with the compressor 160 may not exist and may not be causing the change in the heat rate. As such, a temperature rise ($T_{rise}$) across the hot section 170 is calculated (step 350). Therefore, the calculation is based on the determination of a change in the compressor efficiency or the compressor pressure ratio ($P_{ratio}$). The temperature rise ($T_{rise}$) across the hot section 170 determines if a problem exits with the hot section 170 that is causing the change in heat rate, and the temperature rise ($T_{rise}$) is an indirect measurement of the gas turbine 110 efficiency. In addition, calculation of the temperature rise ($T_{rise}$) across the hot section 170 uses the inputs of turbine exhaust temperature (step 352) and a compressor outlet temperature (step 354). It should be appreciated that the measured data used to calculate the temperature rise ($T_{rise}$) across the hot section 170 are corrected with a correction algorithm, as described above. Also, the temperature rise ($T_{rise}$) across the hot section 170 is calculated by subtracting the turbine exhaust temperature from the compressor outlet temperature.

Once the temperature rise ($T_{rise}$) across the hot section 170 is calculated, a determination is made as to whether a change in the temperature rise ($T_{rise}$) across the hot section 170 exists (step 360). The determination of a change in the temperature rise ($T_{rise}$) across the hot section 170 is made by comparing the calculated temperature rise ($T_{rise}$) across the hot section 170 to the statistical analysis of previously calculated temperature rises ($T_{rise}$) across the hot section 170. If the temperature rise ($T_{rise}$) across the hot section 170 falls outside the control limits of the noise boundaries, a problem may exit with the hot section 170 that is causing the change in the heat rate.

If the temperature rise ($T_{rise}$) across the hot section 170 has not changed, the fuel heat content is calculated (step 370). Therefore, the calculation is based on the determination of a change in the temperature rise ($T_{rise}$). As described above, the fuel heat content is the heating capacity of the fuel used in the combustion turbine system 100. As stated above, the calculation of the fuel heat content uses a calculated value of the heat rate ($HR_{new}$) to a previously calculated value of the heat rate ($HR_{old}$). The fuel heat content FHC is calculated using the following algorithm:

$$\text{FHC (new)} = \frac{\text{HRold}}{\text{HRnew}}$$

It should be appreciated that the measured data used to calculate the fuel heat content (FHC) are corrected using a correction algorithm, as described above.

After the fuel heat content is calculated, a determination is made as to whether the fuel heat content has changed (step 380). The determination of the change in fuel heat content is made by comparing the calculated fuel heat content with a statistical analysis of the previously calculated fuel heat content to determine if the calculated fuel heat content falls outside the control limits of the noise boundaries. If the change in fuel heat content is not determined, the combustion turbine system 100 can have further diagnostic maintenance to determine the cause of the change in the heat rate. If the fuel heat content has changed, the change in the heat rate may be attributable to the change in fuel heat content. As a result, the fuel heat content used in the mathematical model of the operation of the combustion turbine system is changed (step 390). Therefore, the change in the fuel heat content is determined, and the mathematical mode is changed without having to perform unrequired maintenance on the combustion turbine system 100 to determine the cause of the change in the heat rate.

Advantageously, as described herein, a diagnostic tool is provided to determine the cause of a change in the heat rate without performing unrequired maintenance on the combustion turbine system. It should be appreciated that the change in fuel heat content is provided in real time while the combustion turbine system 100 is running. As such, the mathematical model of the operation of the combustion turbine system 100 can be used to adjust the control parameters of the combustion turbine system 100 in real time to maximize the operational efficiency. Therefore, as described herein, a calculated mathematical model is provided with the fuel heat content and any changes in the fuel heat content from conventionally measured data.

The foregoing discussion of the invention has been presented for purposes of illustration and description. Further, the description is not intended to limit the invention to the form disclosed herein. Consequently, variations and modifications commensurate with the above teachings, with the skill and knowledge of the relevant art, are within the scope of the present invention. The embodiment described herein above is further intended to explain the best mode presently known of practicing the invention and to enable others skilled in the art to utilize the invention as such, or in other embodiments, and with the various modifications required by their particular application or uses of the invention. It is intended that the appended claims be construed to include alternative embodiments to the extent permitted by the prior art.

What is claimed is:

1. A method for on-line determination of fuel heat content of fuel used by a combustion turbine system, the fuel heat content being used in a mathematical model of the operation of the combustion turbine system, said method comprising the steps of:

measuring data from said combustion turbine system during combustion of said fuel while said combustion turbine system is on-line and running;

correcting the measured data using a standard correction algorithm;

calculating said fuel heat content of said fuel using at least the corrected data, the calculated fuel heat content being used in the mathematical model of the operation of the combustion turbine system;

comparing the calculated fuel heat content to a statistical record of previously calculated fuel heat contents;

determining a change in said fuel heat content of said fuel based on said step of comparing the calculated fuel heat content to said statistical record of previously calculated fuel heat content; and adjusting the calculated fuel heat content based on the determined change in said fuel heat content, the adjusted calculated fuel heat content being used in the mathematical model of the operation of the combustion turbine system instead of the calculated fuel heat content.

2. The method of claim 1, further comprising the step of determining a heat rate of said combustion turbine system using at least the corrected data wherein the step of calculating said fuel heat content comprises using the calculated heat rate to calculate said fuel heat content.

3. The method of claim 2 wherein:

said step of measuring data comprises:
measuring a flange to flange output and a fuel flow; and
assuming a heat value of said fuel;

said step of correcting the measured data comprises:
correcting said flange to flange output and said fuel flow using said standard correction algorithm;

said step of determining said heat rate comprises:
calculating said heat rate using the corrected flange to flange output, the corrected fuel flow and the assumed heat value;

comparing the calculated heat rate to a statistical record of previously calculated heat rates; and determining a change in said heat rate based on said step of comparing the calculated heat rate to said statistical record of previously calculated heat rates; and adjusting the calculated heat rate based on the determined change in said heat rate wherein the adjusted calculated heat rate is used to calculate said fuel heat content.

4. The method of claim 3, wherein the assumed heat value of said fuel is a low heat value (LHV).

5. The method of claim 1, wherein said standard correction algorithm comprises an International Standards Organization (ISO) algorithm.

6. A method for determining a fuel heat content of fuel used in a combustion turbine system, the fuel heat content being used in a mathematical model of operation of the combustion turbine system, said method comprising the steps of:

measuring data from said combustion turbine system during combustion of said fuel while said combustion turbine system is on-line and running;

correcting the measured data using a standard correction algorithm;

calculating a heat rate using at least a portion of the corrected data;

calculating a first fuel heat content from the calculated heat rate, wherein the calculated first fuel heat content is used in the mathematical model of the operation of the combustion turbine system;

determining an existence of a change in the calculated heat rate wherein the calculated first fuel heat content is used in the mathematical model when the existence of no change in the calculated heat rate is determined;

calculating a compressor efficiency and a pressure ratio using at least a portion of the corrected data when the existence of a change in the heat rate is determined;

determining an existence of a change in the calculated compressor efficiency and the calculated pressure ratio wherein the calculated first fuel heat content is used in the mathematical model when the existence of a change in the calculated compressor efficiency is determined;

calculating a temperature rise across a hot section of said combustion turbine system using at least a portion of the corrected data when the existence of no change in the calculated compressor efficiency is determined;

determining an existence of a change in the calculated temperature rise across said hot section of said combustion turbine system wherein the calculated first fuel heat content is used in the mathematical model when the existence of a change in the calculated temperature rise across the hot section is determined;

determining a change in the calculated first fuel heat content when the existence of no change in the calculated temperature rise across the hot section is determined;

adjusting the calculated first fuel heat content based on the determined change in the calculated first fuel heat content; and using the adjusted calculated first fuel heat content in the mathematical model of the operation of said combustion turbine system instead of the calculated first fuel heat content.

7. The method of claim 6, wherein said step of determining said change in the calculated heat rate comprises comparing the calculated heat rate to a statistical record of previously calculated heat rates.

8. The method of claim 6, wherein said step of determining said change in the calculated compressor efficiency and the calculated pressure ratio comprises:

comparing the calculated compressor efficiency to a statistical record of previously calculated compressor efficiency data; and comparing the calculated pressure ratio to a statistical record of previously calculated pressure ratios.

9. The method of claim 6, wherein said step of determining said change in the calculated temperature rise across said hot section of said combustion turbine system comprises comparing the calculated temperature rise to a statistical record of previously calculated temperature rises.

10. The method of claim 6, wherein said step of determining said change in the calculated first fuel heat content comprises comparing the calculated first fuel heat content to a statistical record of previously calculated fuel heat contents.

11. The method of claim 6, wherein said standard correction algorithm comprises an International Standards Organization (ISO) algorithm.

12. The method of claim 6, wherein said step of adjusting the calculated first fuel heat content based on the determined change in the calculated first fuel heat content comprises calculating a second fuel heat content from the determined change in the calculated first fuel heat content.

* * * * *